United States Patent
Laskar et al.

(10) Patent No.: US 9,468,182 B1
(45) Date of Patent: Oct. 18, 2016

(54) WHEAT VARIETY W040376U1

(71) Applicant: PIONEER HI-BRED INTERNATIONAL, INC., Johnston, IA (US)

(72) Inventors: William Joseph Laskar, Tipton, IN (US); Kyle Jay Lively, Tipton, IN (US); Gregory Charles Marshall, Arcadia, IN (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 14/798,986

(22) Filed: Jul. 14, 2015

(51) Int. Cl.
- *A01H 5/10* (2006.01)
- *A01H 1/02* (2006.01)
- *C12N 5/04* (2006.01)
- *C12N 15/82* (2006.01)
- *A01H 1/08* (2006.01)

(52) U.S. Cl.
CPC *A01H 5/10* (2013.01); *A01H 1/02* (2013.01); *A01H 1/08* (2013.01); *C12N 5/04* (2013.01); *C12N 15/8243* (2013.01); *C12N 15/8245* (2013.01); *C12N 15/8247* (2013.01); *C12N 15/8251* (2013.01); *C12N 15/8271* (2013.01); *C12N 15/8274* (2013.01); *C12N 15/8279* (2013.01); *C12N 15/8286* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 6,825,404 B1 | 11/2004 | Clarkson et al. | |
| 7,291,774 B2 | 11/2007 | Marshall et al. | |
| 9,040,791 B1 * | 5/2015 | Lively | A01H 5/10 800/320.3 |

OTHER PUBLICATIONS

US Plant Variety Protection Certificate No. 200100280 for Wheat Variety 25R78; issued Apr. 18, 2002.
US Plant Variety Protection Certificate No. 200500152 for Wheat Variety 25R51; issued Mar. 6, 2006.

* cited by examiner

*Primary Examiner* — Cynthia Collins
(74) *Attorney, Agent, or Firm* — Pioneer Hi-Bred Int'l, Inc.

(57) ABSTRACT

A wheat variety designated W040376U1, the plants and seeds of wheat variety W040376U1, methods for producing a wheat plant produced by crossing the variety W040376U1 with another wheat plant, and hybrid wheat seeds and plants produced by crossing the variety W040376U1 with another wheat line or plant, and the creation of variants by mutagenesis or transformation of variety W040376U1. This invention also relates to methods for producing other wheat varieties or breeding lines derived from wheat variety W040376U1 and to wheat varieties or breeding lines produced by those methods.

20 Claims, No Drawings

WHEAT VARIETY W040376U1

FIELD OF INVENTION

This invention is in the field of wheat (*Triticum aestivum* L.) breeding, specifically relating to a wheat variety designated W040376U1.

BACKGROUND OF INVENTION

There are numerous steps involving significant technical human intervention in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These traits may include, but are not limited to higher seed yield, resistance to diseases and/or insects, tolerance to drought and/or heat, altered milling properties, abiotic stress tolerance, improvements in compositional traits, and better agronomic characteristics.

Processes which lead to the final step of marketing and distribution can take from approximately six to twelve years of significant technical human intervention starting from the time the first cross is made. Therefore, development of new varieties is a time-consuming process that requires precise forward planning, efficient use of resources, and a minimum in changes of direction. Stable, high yielding wheat varieties that are agronomically sound and which maximize the amount of grain produced on the land used are selected and developed to provide superior wheat plant varieties. Significant human intervention is required.

Wheat is grown worldwide and is the most widely adapted cereal. There are five main wheat market classes. They include the four common wheat (*Triticum aestivum* L.) classes: hard red winter, hard red spring, soft red winter, and white. The fifth class is durum (*Triticum turgidum* L.). Common wheats are used in a variety of food products such as bread, cookies, cakes, crackers, and noodles. In general the hard wheat classes are milled into flour used for breads and the soft wheat classes are milled into flour used for pastries and crackers. Wheat starch is also used in the paper industries, as laundry starches, and in other products.

SUMMARY OF THE INVENTION

In certain embodiments, a plant, plant part, seed, or plant cell of wheat variety W040376U1 is provided, representative seed of variety W040376U1 having been deposited with the ATCC.

In certain embodiments, wheat seed is provided from the cross of the plant or plant part of wheat variety W040376U1 with a different wheat plant or plant part. Plants and plant parts grown from the seed of the cross are also provided. Methods for producing different wheat plants are provided in which plant breeding techniques are applied to the wheat plant or plant part grown from the seed of the cross.

In certain embodiments, methods for producing progeny seed and the progeny seed so made are provided in which a wheat plant produced by growing a seed of the cross of wheat variety W040376U1 with a different wheat plant or plant part is then crossed to a plant of wheat variety W040376U1. Methods and backcrossed seed are also provided in which the progeny seed is grown and crossed to a plant wheat variety W040376U1 to produce backcrossed seed.

In certain embodiments, methods for producing double haploid wheat plants are provided in which a wheat plant produced by growing a seed of the cross of wheat variety W040376U1 with a different wheat plant or plant part is then crossed with another plant to form haploid cells. The chromosomes of the haploid cells are doubled to form double haploid cells which are grown into a double haploid wheat plant or plant part.

In certain embodiments, methods for cleaning, conditioning, or applying a seed treatment to the seed of wheat variety W040376U1 are provided.

In certain embodiments, methods of milling the seed of wheat variety W040376U1 and the flour produced from such milling is provided. The flour may include a cell of wheat variety W040376U1.

In certain embodiments, a tissue culture of cells is provided which are produced from the plant, plant part, seed or cell of wheat variety W040376U1. Plants and plant parts regenerated from the tissue culture are also provided.

In certain embodiments, wheat plants are provided which plants include a transgene and which were produced by transforming the plant, plant part, seed or cell of wheat variety W040376U1.

In certain embodiments, a plant, plant part, seed, or plant cell of wheat variety W040376U1 further comprising a locus conversion is provided. The plant, plant part, seed, or plant cell may have other than the locus conversion essentially all of the morphological and physiological characteristics of wheat variety W040376U1. The locus conversion may confer a trait selected from male sterility, abiotic stress tolerance, altered phosphorus, altered antioxidants, altered fatty acids, altered essential amino acids, altered carbohydrates, herbicide resistance, insect resistance, disease resistance or a combination thereof.

In certain embodiments, methods for producing a wheat plant are provided in which plant breeding techniques are applied to a wheat plant grown from seed of wheat variety W040376U1 comprising a locus conversion, or to a plant grown from seed of a cross of such a wheat plant to a different wheat plant.

DETAILED DESCRIPTION

The present invention relates to a new and distinctive wheat (*Triticum aestivum* L.), variety designated W040376U1, which has been the result of years of careful breeding and selection in a comprehensive wheat breeding program.

The modified pedigree selection method of breeding was used to derive this line from elite germplasm. The first cross was made in 2003 and breeding and selection continued until 2014. W040376U1 represents a significant advancement in elite germplasm adapted to the United States.

Field crops are bred through techniques that take advantage of the plant's method of pollination, such as self-pollination, sib-pollination or cross-pollination. As used herein, the term cross-pollination includes pollination with pollen from a flower on a different plant from a different family or line and does not include self-pollination or sib-pollination. Wheat plants (*Triticum aestivum* L.), are recognized to be naturally self-pollinated plants which, while capable of undergoing cross-pollination, rarely do so in nature. Thus intervention for control of pollination is needed for the establishment of superior varieties.

Provided are methods of producing progeny with a new combination of genetic traits by cross pollinating one wheat plant with another by emasculating flowers of a designated female plant and pollinating the female parent with pollen from the designated male parent. Suitable methods of cross-pollination of wheat plants are described, for example, in U.S. Pat. No. 8,809,654, which is herein incorporated by reference, but other methods can be used, or modified, as is known to those skilled in the art.

A cross between two different homozygous lines produces a uniform population of hybrid plants that may be heterozygous for many gene loci. A cross of two heterozygous plants each that differ at a number of gene loci will produce a population of plants that differ genetically and will not be uniform. Regardless of parentage, plants that have been self-pollinated and selected for type for many generations become homozygous at almost all gene loci and produce a uniform population of true breeding progeny. The term "homozygous plant" is hereby defined as a plant with homozygous genes at 95% or more of its loci.

Choice of breeding or selection methods depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection can be based on mean values obtained from replicated evaluations of families of related plants. Popular selection methods commonly include pedigree selection, modified pedigree selection, mass selection, and recurrent selection.

The complexity of inheritance influences choice of the breeding method. For example, pedigree breeding, backcross breeding, single seed descent, and bulk breeding, which are each described in U.S. Pat. No. 8,809,654 (incorporated herein by reference), can be used. Each wheat breeding program may include a periodic, objective evaluation of the efficiency of the breeding procedure. Evaluation criteria vary depending on the goal and objectives, but may include gain from selection per year based on comparisons to an appropriate standard, overall value of the advanced breeding lines, and number of successful varieties produced per unit of input (e.g., per year, per dollar expended, etc.).

Various recurrent selection techniques can be used to improve quantitatively inherited traits controlled by numerous genes. The use of recurrent selection in self-pollinating crops depends on the ease of pollination and the number of hybrid offspring from each successful cross. Recurrent selection can be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued. Plants from the populations can be selected and selfed to create new varieties.

Wheat variety W040376U1 can be used as the female or the male parent in biparental crosses in order to develop new and valuable wheat varieties. Wheat normally self-pollinates in nature. Wheat cross-pollination can be achieved by emasculating a designated female plant and pollinating the female plant with pollen from the designated male parent.

In order to cross pollinate one wheat plant with another to produce progeny with a new combination of genetic traits, a method of cross-pollination is employed. Cross-pollination is known to those skilled in the art. Wheat cross-pollination is achieved by emasculating flowers of a designated female plant and pollinating the female parent with pollen from the designated male parent. The following method was employed to cross-pollinate the wheat plants, but other methods can be used, or modified, as is known to those skilled in the art.

The designated female wheat plant is emasculated before its anthers shed pollen to avoid self-pollination. Emasculation is done by selecting an immature spike on the designated female parent plant that has not started to bloom and shed any viable pollen. Each spike consists of a series of spikelets composed of florets which each contain one ovary with a feathery stigma and three anthers. Typically all but the two primary florets are removed from each spikelet by using tweezers. The glumes of each remaining floret can be trimmed back about 50% using scissors to expose the immature anthers. The tweezers are used to spread the glumes slightly open while at the same time surrounding the anthers. The anthers can then be removed by gently grabbing and pulling them out of the flower with the tweezers in an upward motion. With skill, all three anthers can be removed at once, but this must be confirmed visually before moving to the next flower. Repeated attempts to remove any remaining anthers increases the risk of damage to the stigma and ovary and greatly reduce the frequency of cross-pollination. After all the florets are emasculated on a spike, it is covered with a cellophane bag to prevent pollination with stray pollen from surrounding plants. One to three days after the female spike is emasculated a mature spike that is shedding pollen is selected from the designated male plant for cross-pollination using the approach method. The stem of the male spike is cut off at least one foot below the spike and typically the glumes of all the spikelets are trimmed back with scissors to encourage anther extrusion during pollination. The stem of the male spike is placed in a test tube full of water, which is attached to a stick implanted beside the emasculated female spike. The male spike is placed above the emasculated female spike(s) in the same cellophane bag and it is permitted to shed pollen naturally over the next several days. By waiting a few days after emasculation, one can ensure that no anthers or viable pollen has remained in the female spike and the stigmas become more receptive to cross-pollination. Emasculated female spikes that are effectively cross-pollinated by the designated male parent will typically set 10-30 seeds per spike. Depending on the breeding objectives, one to five spikes are typically cross-pollinated for each cross. Spikes from the cross are hand harvested and the F1 seed from the spikes are advanced to the F1 generation. The F1 plants can be used for used for subsequent cross-pollination or they can be advanced to the F2 generation for selection and further advancement. For the F2 grow out, 2500 to 3500 seeds are typically planted.

Plant breeding methods may include use of molecular markers, including techniques such as Starch Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), Single Nucleotide Polymorphisms (SNPs) and Quantitative Trait Loci (QTL) mapping.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection.

The production of double haploids can also be used for the development of homozygous lines in the breeding program and in the production of, for example, hybrid wheat. In an embodiment, the variety is used in the production of hybrid wheat. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. Hybrid wheat can be produced, for example, with the help of cytoplasmic male sterility, nuclear genetic male sterility, chemicals or a combination thereof.

A breeder uses various methods to help determine which plants should be selected from the segregating populations and ultimately which lines will be used for commercialization. In addition to the knowledge of the germplasm and other skills the breeder uses, a part of the selection process is dependent on experimental design coupled with the use of statistical analysis. Experimental design and statistical analysis can be used to help determine which plants, which family of plants, and finally which lines are significantly better or different for one or more traits of interest. Experimental design methods can be used to control error so that differences between two lines can be more accurately determined. Statistical analysis includes the calculation of mean values, determination of the statistical significance of the sources of variation, and the calculation of the appropriate variance components. Five and one percent significance levels are customarily used to determine whether a difference that occurs for a given trait is real or due to the environment or experimental error.

Plant breeding is the genetic manipulation of plants. The goal of wheat breeding is to develop new, unique and superior wheat varieties. In practical application of a wheat breeding program, the breeder initially selects and crosses two or more parental lines, followed by repeated selfing and selection, producing many new genetic combinations. The breeder can theoretically generate billions of different genetic combinations via crossing, selfing and mutations. Each year, the plant breeder selects the germplasm to advance to the next generation. This germplasm is grown under unique and different geographical, climatic and soil conditions and further selections are then made during and at the end of the growing season.

Plants are tested to detect major faults and establish the level of superiority or improvement over current varieties. Research and development, breeding and testing processes, which lead to the final step of marketing and distribution, can take from six to twelve years from the time the first cross is made. Therefore, development of new varieties is a time-consuming process that requires precise forward planning, efficient use of resources, and a minimum of changes in direction.

According to the invention, there is provided a novel wheat variety, designated W040376U1 and processes for making W040376U1. This invention relates to seed of wheat variety W040376U1, to the plants of wheat variety W040376U1, to plant parts of wheat variety W040376U1, and to processes for making a wheat plant that comprise crossing wheat variety W040376U1 with another wheat plant. This invention also relates to processes for making a wheat plant containing in its genetic material one or more traits introgressed into W040376U1 through backcross conversion and/or transformation, and to the wheat seed, plant and plant parts produced thereby. This invention also relates to the creation of variants by mutagenesis or transformation of wheat W040376U1. This invention further relates to a hybrid wheat seed, plant or plant part produced by crossing the variety W040376U1 or a locus conversion of W040376U1 with another wheat variety.

Wheat varieties that are highly homogeneous, homozygous and reproducible are useful as commercial varieties. There are many analytical methods available to determine the homozygotic stability, phenotypic stability, and identity of these varieties.

In some embodiments, data can be collected from the observation of phenotypic traits over the life of the wheat plants in field experiments. Phenotypic characteristics observed can include traits such as seed yield, head configuration, glume configuration, seed configuration, lodging resistance, disease resistance, maturity. The genotype of a plant can also be examined. There are many laboratory-based techniques available for the analysis, comparison and characterization of plant genotype including, without limitation, Gel Electrophoresis, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). Gel electrophoresis is particularly useful in wheat. Wheat variety identification can occur, for example, through electrophoresis of gliadin, glutenin, albumin and globulin, and total protein extracts.

Wheat variety W040376U1 has shown uniformity and stability for all traits, as described in the following variety description information. It has been self-pollinated a sufficient number of generations, with careful attention to uniformity of plant type to ensure homozygosity and phenotypic stability. The line has been increased with continued observation for uniformity. No variant traits have been observed or are expected in W040376U1, as described in Table 1B.

Wheat variety W040376U1 is a common, soft red winter wheat. Variety W040376U1 demonstrates excellent yield potential with very good test weight, excellent resistance to *Fusarium* head blight (scab), and very good resistance to stripe rust. Variety W040376U1 has medium maturity relative to other varieties in the primary region of adaptation. It has shown adaptation to the northern soft wheat regions based on tests conducted in Arkansas, Georgia, Illinois, Indiana, Kentucky, Michigan, Missouri, Mississippi, North Carolina, Ohio, Virginia, and Ontario, Canada.

Wheat variety W040376U1 was developed by from a cross between three homozygous lines Bess, 25R78, and 25R51. Wheat variety W040376U1, being substantially homozygous, can be reproduced by planting seeds of the line, growing the resulting wheat plants under self-pollinating or sib-pollinating conditions, and harvesting the resulting seed, using techniques familiar to the agricultural arts.

Wheat variety W040376U1 is a soft red winter wheat (*Triticum aestivum* L.) derived from a three parent cross made in 2003 as follows:

Bess/25R78//25R51

The single cross Bess/25R78 was made during the 2003 spring greenhouse cycle. The final cross was made in the 2003 fall greenhouse cycle. This and the subsequent breeding history of W040376U1 are described below.

| Year | Generation | |
|---|---|---|
| 2003 | Final cross | Final cross made in greenhouse |
| 2004 | F1 | F1 transplanted into field nursery |
| 2005 | F2 | F2 bulk population grown in Ontario Canada |
| 2006 | F3 | F3 bulk population grown in Ontario Canada |
| 2007 | F4 | F4 headrows from F3 plant selections grown in Indiana |
| 2008 | F5 | F5 bulks from selected F4 rows grown at two locations |
| 2009 | F6 | F6 headrows from F5 plant selections grown at two locations |
| 2010 | F7 | F7 preliminary yield testing |
| 2011 | F8 | F8 advanced yield testing and headrow purification/increase |
| 2012 | F9 | F9 elite yield testing and headrow purification/increase |
| 2013 | F10 | F10 elite yield testing and progeny plot purification/increase |

During the process of development, the plant populations as well as individual plants are evaluated for general health, agronomics, and stability at many stages. These evaluations typically include, but are not limited to, one or more of the following characteristics: plant architecture traits such as seedling coleoptile length, coleoptile color (presence of anthocyanin), juvenile plant growth habit, tillering, plant height, straw strength or lodging, flag leaf carriage at boot stage, leaf width and length, glaucosity of stems, leaves and spikes, pubescence of leaves and spikes, spike shape, spike density, spike awnedness, and plant color through-out stages of growth; plant growth characteristics, such as vernalization requirement, date for first stem joint emergence, heading date, flowering date, physiological maturity date and harvest maturity; tolerance to weather conditions, such as cold tolerance, resistance to heaving, tolerance to wet soils and standing water, drought and heat tolerance; and grain characteristics, such as grain yield, test weight, 1000 kernel weight, grain moisture, grain color, grain shape, grain protein, flour milling yield and baking characteristics.

During its development, wheat variety W040376U1 was assayed and/or planted in field trials and evaluated for a variety of traits and/or characteristics as compared to check varieties. The property(s) of appropriate check varieties include but are not limited to varieties with a similar relative maturity, varieties known to be susceptible to one or more particular diseases, insect, pathogen, field condition, weather condition, soil type or condition, and/or crop management practice, varieties known to be tolerant or resistant to one or more particular diseases, insect, pathogen, field condition, weather condition, soil type or condition, and/or crop management practice, varieties comprising one or more particular marker locus, and/or varieties derived from another appropriate variety or having a particular pedigree. Appropriate choice of check varieties for comparison assures an appropriate baseline and valid qualitative or quantitative assessment of any test varieties.

Throughout the course of the development of W040376U1, the plants can be tested for various traits including, but not limited to grain yield, test weight, heading date, harvest maturity, plant height, straw strength, pre-harvest sprout tolerance, resistance levels to leaf rust, stripe rust, tan spot, *Septoria tritici* blotch, *Stagnospora nodorum* blotch, powdery mildew, *Fusarium* (scab), wheat yellow mosaic virus and soilborne mosaic virus, and grain characteristics such as flour yield, flour protein, and baking characteristics.

The cultivar W040376U1 was bred and selected using a modified pedigree selection method for any and all of the following characteristics in the field environment: disease resistance, plant type, plant height, head type, straw strength, maturity, grain yield, test weight, and milling and baking characteristics. W040376U1 has been shown to be uniform and stable since the $7^{th}$ generation, or for the last 4 generations. W040376U1 has shown no variants other than what would normally be expected due to environment.

Wheat variety W040376U1, being substantially homozygous, can be reproduced by planting seeds of the line, growing the resulting wheat plants under self-pollinating or sib-pollinating conditions, and harvesting the resulting seed, using techniques familiar to the agricultural arts.

When referring to area of adaptability, such term is used to describe the location with the environmental conditions that would be well suited for this wheat variety. Area of adaptability is based on a number of factors, for example: days to heading, winter hardiness, insect resistance, disease resistance, and drought resistance. Area of adaptability does not indicate that the wheat variety will grow in every location within the area of adaptability or that it will not grow outside the area. Northern area=States of DE, IL, IN, MI, MO, NJ, NY, OH, PA, WI and Ontario, Canada
Mid-south=States of AR, KY, MO Bootheel and TN
Southeast=States of NC, SC, and VA
Deep South=States of AL, GA, LA, and MS
Table 1A lists common traits and a description of how the trait is scored.

TABLE 1A

| TRAIT | DESCRIPTION & HOW SCORED |
|---|---|
| HD DAT | Heading Date in days past Jan. 1st); plot dated on the day when approximately 50% of the heads are 50% out of the boot |
| HGTIN HGTCM | Height (inches or centimeters); scored with a measuring stick after all genotypes fully extended; wheat gathered around stick and average distance to the top of the heads is noted; 2-3 samplings per plot |
| LF BLT | Leaf Blight Complex; score based on amount of infection on flag and flag -1 leaves; typical scale:<br>% of uninfected leaf surface area<br>flag    flag    -1<br>9 -    100%    100%<br>8 -    100%    75%<br>7 -    100%    50%<br>6 -    >90%    <50%<br>5 -    75-90%    <25%<br>4 -    50-74%    —<br>3 -    23-49%    —<br>2 -    10-24%    —<br>1 -    0-9% |
| LF RST | Leaf Rust; score based on amount of infection evident on flag leaves; typical scale:<br>9 - clean<br>8 - trace amounts<br>7 - <5% flag leaf area infected<br>6 - 6-10% flag leaf area infected<br>5 - 11-20% flag leaf area infected<br>4 - 21-30% flag leaf area infected<br>3 - 31-40% flag leaf area infected<br>2 - 41-50% flag leaf area infected<br>1 - over 50% flag leaf area infected |
| MAT | Maturity; used on larger, earlier generation tests in the place of heading date; scale based on maturity of known checks and will vary from year to year based on when the note is taken; typical scale: |

TABLE 1A-continued

| TRAIT | DESCRIPTION & HOW SCORED |
|---|---|
| | 9 - very late, boot not swelling when note is taken |
| | 8 - still in boot when note is taken |
| | 7 - splitting boot, will head two days after note is taken |
| | 6 - will head day after the note is taken |
| | 5 - headed on the day note is taken |
| | 4 - headed day before note taken |
| | 3 - headed two days before note taken |
| | 2 - fully extended, some flowering visible |
| | 1 - extended and flowering |
| | Maturity may also be scored at physiological maturity; typical scaler: |
| | 9 - ready to be harvested |
| | 7 - caryopse hard to divide |
| | 5 - head yellowing an day note is taken |
| | 3 - grain still at doughstage |
| | 1 - head completely green |
| PM | Powdery Mildew; score based on severity of infection and progression of the disease up the plant; scale based on reaction of known checks with attention given to race changes; typical scale: |
| | 9 - clean |
| | 8 - trace amount low on plants |
| | 7 - slight infection mostly low on plants |
| | 6 - moderate infection low on plants; trace amounts on flag −1 leaves |
| | 5 - moderate infection low on plants, moderate amounts on flag −1 leaves |
| | 4 - moderate infection through canopy with trace amounts evident on flag leaves |
| | 3 - severe infection through canopy with up to 25% infection on flag leaves |
| | 2 - severe infection through canopy with up to 50% infection on flag leaves |
| | 1 - severe infection; greater than 50% infection on flag leaves |
| SB MV | Soil Borne Mosaic Virus; score based on amount of mottling, ohlorosis, and/or stunting; scale based on reaction of known checks; typical scale |
| | 1 - severe stunting to the point of rosettes |
| | 2 - severe stunting |
| | 3 - very chlorotic with moderate stunting |
| | 4 - very chlorotic with mild stunting |
| | 5 - moderate mottling with no stunting |
| | 6 - mottling evident |
| | 7 - mottling barely visible |
| | 8 - green, very little mottling |
| | 9 - green, no mottling visible |
| SHTSC | Shattering score. Scores are based on the amount of grain that is visible in the spike just before harvest. |
| | 9 - grain no visible in the spike, Glumes closed. |
| | 8 - Glumes slightly opened in <10% of the grains. |
| | 7 - Glumes slightly opened in >10% of the grains. |
| | 6 - Glumes moderately opened in <20% of the grains. |
| | 5 - Glumes moderately opened in >20% of the grains. |
| | 4 - Glumes completely opened in <30% of the grains. |
| | 3 - Glumes completely opened in >30% of the grains. |
| | 2 - 20%-50% of the grain on the soil |
| | 1 - >50% of the grain on the soil. |
| SS MV | Spindle Streak Mosaic Virus; score based on amount of mottling and chlorosis; scale based on reaction of known checks; scale similar to SS MV with less emphasis on stunting |
| ST EDG | Straw Lodging; score based on amount of lodging; typical scale: |
| | 9 - still upright |
| | 8 - only slight leaning |
| | 7 - some leaning, no lodging |
| | 6 - moderate leaning, little lodging |
| | 5 - up to 10% lodged |
| | 4 - 11-25% lodged |
| | 3 - 26-50% lodged |
| | 2 - 51-75% lodged |
| | 1 - greater than 75% lodged |
| STPRST | Stripe rust. Stripe rust is an important disease that occurs most often in Europe. The infection may only affect the flag leaf, or it may attack the entire plant including the head. Two scales based on level of infection included below: |
| | Score based on the amount of infection of the whole plant! |
| | 9 - clean |
| | 8 - traces |
| | 7 - <5% plant infected |
| | 6 - 10% plant infected |
| | 5 - 20% plant infected |
| | 4 - 40% plant infected |
| | 3 - 60% plant infected |
| | 2 - 60% plant infected head rusted |
| | 1 - Plant not able to produce kernel |
| | Score based on the amount and type of infection evident on flag leaves: |
| | 9 - clean |
| | 8 - trace amounts (Chlorotic-necrotic freckles) |
| | 7 - <5% flag leaf area infected |
| | 6 - 6-10% flag leaf area infected (chlorotic-necrotic stripes). |
| | 5 - 11-20% flag leaf area infected (chlorotic-necrotic stripes). |
| | 4 - 21-30% flag leaf area infected (chlorotic-necrotic stripes). |
| | 3 - 31-40% flag leaf area infected (chlorotic-necrotic stripes). |
| | 2 - 41-50% flag leaf area infected (some chlorosis). |
| | 1 - over 50% flag leaf area infected (no chlorosis). |
| UNI | Uniformity; used to determine how pure a line is generally at the F7 (pre-advanced) generation; typical scale: |
| | 9 - very uniform in all aspects |
| | 8 - good uniformity |
| | 7 - fairly uniform, but some off-types |
| | 6 - several off-types, but can be cleaned up with normal purification procedures |
| | 5 - several off-types, will be a challenge to clean up with normal purification procedures |
| | 4 - considerable number of off-types; will need to be reselected to proceed as a pureline |
| | 3 - as many as 25% off types; will need to be reselected |
| | 2 - as many as 50% off types; will need to be reselected |
| | 1 - more than 50% off types; what you have here is a problem |
| WNTHRD | Winter Hardiness; score based on amount of brownback and kill; best scored at time of early spring regrowth; typical scale: |
| | 9 - very green, no brown-back |
| | 8 - green, slight brown-back |
| | 7 - moderate brown-back |
| | 6 - hard brown-back, no kill |
| | 5 - hard brown-back with less than 10% kill |
| | 4 - 11-25% kill |
| | 3 - 26-50% kill |
| | 2 - 51-75% kill |
| | 1 - greater than 75% kill |
| SC AB | fusarium head scab; score based on visual evaluation of the percentage of scab infected heads on a whole plot basis with consideration given to both total heads affected and severity of infection; typical scale: |
| | 9 - no scab infection |
| | 8 - trace amount (1-2%) with infections limited to individual spikelets |
| | 7 - up to 5% infection with most infection limited to less than 50% of the spike |
| | 6 - 5-15% of heads infected |
| | 5 - 15-30% of heads infected |
| | 4 - 30-50% of heads infected |
| | 3 - 50-75% of heads infected |
| | 2 - 75-90% of heads infected |
| | 1 - >90% of heads infected |
| | most genotypes scoring 5 or below would typically have the majority of the spike infected |

TABLE 1B

VARIETY DESCRIPTION INFORMATION
W040376U1

1. KIND: 1 (1 = Common, 2 = Durum, 3 = Club, 4 = Other)
2. VERNALIZATION: 2 (1 = Spring, 2 = Winter, 3 = Other)
3. COLEOPTILE ANTHOCYANIN: 1 (1 = Absent, 2 = Present)
4. JUVENILE PLANT GROWTH: 2 (1 = Prostrate, 2 = Semi-erect, 3 = Erect)

TABLE 1B-continued

VARIETY DESCRIPTION INFORMATION
W040376U1

5. PLANT COLOR (boot stage): 2 (1 = Yellow-Green, 2 = Green, 3 = Blue-Green)
6. FLAG LEAF (boot stage): 2 (1 = Erect, 2 = Recurved)
   FLAG LEAF (boot stage): 2 (1 = Not Twisted, 2 = Twisted)
   FLAG LEAF (boot stage): 2 (1 = Wax Absent, 2 = Wax Present)
7. EAR EMERGENCE: 124 = Number of Days after Jan. 1 and Same day as 25R47
8. ANTHER COLOR: 1 (1 = Yellow, 2 = Purple)
9. PLANT HEIGHT (from soil to top of head, excluding awns): 91.4 cm (Average) 5 cm Taller Than 25R47
10. STEM:
    A. ANTHOCYANIN: 1 (1 = Absent, 2 = Present)
    B. WAXY BLOOM: 2 (1 = Absent, 2 = Present)
    C. HAIRINESS (last internode of rachis): 2 (1 = Absent, 2 = Present)
    D. INTERNODE: 1 (1 = Hollow, 2 = Semi-solid, 3 = Solid)
    E. PEDUNCLE: 2 (1 = Erect, 2 = Recurved, 3 = Semi-erect)
    F. AURICLE
       Anthocyanin: 2 (1 = Absent, 2 = Present)
       Hair: 2 (1 = Absent, 2 = Present)
11. HEAD (at maturity)
    A. DENSITY: 3 (1 = Lax, 2 = Middense, 3 = Dense)
    B. SHAPE: 1 (1 = Tapering, 2 = Strap, 3 = Clavate, 4 = Other)
    C. CURVATURE: 3 (1 = Erect, 2 = Inclined, 3 = Recurved)
    D. AWNEDNESS: 4 (1 = Awnless, 2 = Apically Awnletted, 3 = Awnletted 4 = Awned)
12. GLUMES (at Maturity):
    A. COLOR: 3 (yellow) (1 = White, 2 = Tan, 3 = Other)
    B. SHOULDER: 2 (1 = Wanting, 2 = Oblique, 3 = Rounded, 4 = Square, 5 = Elevated, 6 = Apiculate)
    C. SHOULDER WIDTH: 2 (1 = Narrow, 2 = Medium, 3 = Wide)
    D. BEAK: 3 (1 = Obtuse, 2 = Acute, 3 = Acuminate)
    E. BEAK WIDTH: 2 (1 = Narrow, 2 = Medium, 3 = Wide)
    F. GLUME LENGTH: 3 (1 = Short (ca. 7 mm), 2 = Medium (ca. 8 mm), 3 = Long (ca. 9 mm))
    G. GLUME WIDTH: 2 (1 = Narrow (ca. 3 mm), 2 = Medium (ca. 3.5 mm), 3 = Wide (ca. 4 mm)
    H. PUBESCENCE: 1 (1 = Not Present 2 = Present)
13. SEED:
    A. SHAPE: 1 (1 = Ovate, 2 = Oval, 3 = Elliptical)
    B. CHEEK: 1 (1 = Rounded, 2 = Angular)
    C. BRUSH : 2 (1 = Short, 2 = Medium, 3 = Long)
       BRUSH: 1 (1 = Not Collared, 2 = Collared)
    D. CREASE: 2 (1 = Width 60% or less of Kernel, 2 = Width 80% or less of Kernel, 3 = Width Nearly as Wide as Kernel)
       CREASE: 1 (1 = Depth 20% or less of Kernel, 2 = Depth 35%, or less of Kernel, 3 = Depth 50% or less of Kernel)
    E. COLOR: 3 (1 = White, 2 = Amber, 3 = Red, 4 = Other)
    F. TEXTURE: 2 (1 = Hard, 2 = Soft, 3 = Other)
    G. PHENOL REACTION: 3 (1 = Ivory, 2 = Fawn, 3 = Light Brown, 4 = Dark Brown 5 = Black)
    H. SEED WEIGHT: 35 g/1000 Seed
    I. GERM SIZE: 1 (1 = Small, 2 = Midsize, 3 = Large)
14. DISEASE: (0 = Not tested, 1 = Susceptible, 2 = Resistant, 3 = Intermediate, 4 = Tolerant)
    SPECIFIC RACE OR STRAIN TESTED
    Stem Rust (*Puccinia graminis* f. sp. *tritici*) 0
    Leaf Rust (*Puccinia recondita* f. sp. *tritici*) 3
    Stripe Rust (*Puccinia striiformis*) 3
    Loose Smut (*Ustilago tritici*) 0
    Powdery Mildew (*Erysiphe graminis* f. sp. *tritici*) 3
    Common Bunt (*Tilletia tritici* or *T. laevis*) 0
    Dwarf Bunt (*Tilletia controversa*) 0
    Karnal Bunt (*Tilletia indica*) 0
    Flag Smut (*Urocystis agropyri*) 0
    Tan Spot (*Pyrenophora tritici-repentis*) 3
    Halo Spot (*Selenophoma donacis*) 0
    *Septoria* spp. 3
    *Septoria nodorum* (Glume Blotch) 0
    *Septoria avenae* (Speckled Leaf Disease) 0
    *Septoria tritici* (Speckled Leaf Blotch) 3
    Scab (*Fusarium* spp.) 2
    "Snow Molds" 0
    Kernel Smudge ("Black Point") 0
    Common Root Rot (*Fusarium*, *Cochliobolus* and *Bipolaris* spp.) 0
    Barley Yellow Dwarf Virus (BYDV) 0
    *Rhizoctonia* Root Rot (*Rhizoctonia solani*) 0
    Soilborne Mosaic Virus (SBMV) 1
    Black Chaff (*Xanthomonas campestris* pv. *translucens*). 0
    Wheat Yellow (Spindle Streak) Mosaic Virus 0
    Bacterial Leaf Blight (*Pseudomonas syringae* pv. *syringae*) 0
    Wheat Streak Mosaic Virus (WSMV) 0
15. INSECT: (0 = Not tested, 1 = Susceptible, 2 = Resistant, 3 = Intermediate, 4 = Tolerant)
    Stem Sawfly (*Cephus* spp.) 0
    Cereal Leaf Beetle (*Oulema melanopa*) 0
    Russian Aphid (*Diuraphis noxia*) 0
    Greenbug (*Schizaphis graminum*) 0
    Aphids (Specify) 0
    Hessian Fly (*Mayetiola destructor*) Biotype L 1
    Hessian Fly (*Mayetiola destructor*) Field 1

In one aspect, wheat plants, plant parts and seeds are provided which have all or essentially all of the characteristics set forth in Table 1B. In one aspect wheat plants, plant parts and seeds are provided which have all or essentially all of the physiological and morphological characteristics of wheat variety W040376U1, representative seed having been deposited with the ATCC as disclosed herein.

Wheat variety W040376U1 can be further reproduced by tissue culture and regeneration. Tissue culture of various tissues of wheat and regeneration of plants therefrom is well known and widely published. Thus, in another aspect provided are cells which upon growth and differentiation produce wheat plants capable of having the physiological and morphological characteristics of wheat variety W040376U1.

As used herein, the term "plant parts" includes, without limitation, plant protoplasts, plant cell tissue cultures from which wheat plants can be regenerated, plant calli, plant clumps, plant cells, embryos, pollen, ovules, pericarp, seed, flowers, florets, heads, spikes, leaves, roots, root tips, anthers, and the like. When indicating that a plant is crossed or selfed this indicates that any plant part of the plant can be used. For instance the plant part does not need to be attached to the plant during the crossing or selfing, only the pollen might be used.

In one aspect, a wheat plant containing a locus conversion or an essentially derived variety of W040376U1 is provided. As determined by the UPOV Convention, essentially derived varieties may be obtained for example by the selection of a natural or induced mutant, or of a somaclonal variant, the selection of a variant individual from plants of the initial variety, backcrossing, or transformation by genetic engineering. An essentially derived variety of W040376U1 is further defined as one whose production requires the repeated use of variety W040376U1 or is predominately derived from variety W040376U1. International Convention for the Protection of New Varieties of Plants, as amended on Mar. 19, 1991, Chapter V, Article 14, Section 5(c).

A locus conversion refers to plants within a variety that have been modified in a manner that retains the overall genetics of the variety and further comprises one or more loci with a specific desired trait, such as male sterility, insect, disease or herbicide resistance. Examples of single locus conversions include mutant genes, transgenes and native traits finely mapped to a single locus. One or more locus conversion traits may be introduced into a single wheat variety. As used herein, the phrase 'comprising a' transgene, transgenic event or locus conversion means one or more transgenes, transgenic events or locus conversions.

Any DNA sequences, whether from a different species or from the same species that are inserted into the genome using transformation are referred to herein collectively as "transgenes". Methods for producing transgenic plants and in particular embodiments, transformed versions of the wheat variety W040376U1 and methods for producing such plants are provided.

Numerous methods for plant transformation have been developed, including biological protocols, such as using *Agrobacterium*, and physical techniques, such as biolistics and direct gene transfer. In addition, expression vectors and in vitro culture methods for plant cell or tissue transformation and regeneration of plants are available. The most prevalent types of plant transformation involve the construction of an expression vector. Such a vector comprises a DNA sequence that contains a gene or coding sequence under the control of or operatively linked to a regulatory element, such as a promoter. The vector may contain one or more genes or coding sequences and one or more regulatory elements. The regulatory element or promoter can be heterologous to the gene or coding sequence.

Various elements can be introduced into the plant genome, including but are not limited to genes; coding sequences; inducible, constitutive, and tissue specific promoters; enhancing sequences; and signal and targeting sequences. As used herein, when used in transformation, a gene generally references the coding sequence or cDNA which does not include intron sequences not encoding a polypeptide.

A genetic trait, engineered into a particular wheat plant using transformation techniques, can be moved into another line using traditional breeding techniques that are well known in the plant breeding arts. For example, a backcrossing approach can be used to move a transgene from a transformed wheat plant to an elite wheat variety to provide resulting progeny comprising a transgene. As used herein, "crossing" can refer to a simple X by Y cross, or the process of backcrossing, depending on the context. The term "breeding cross" excludes the processes of selfing or sibbing.

Transgenic wheat plants according to the present invention can be harvested to produce a foreign protein in commercial quantities. The foreign protein can be extracted from a tissue of interest, such as a seed, or from total biomass by known methods. The approximate chromosomal location of the integrated DNA molecule can be determined from a genetic map generated, for example, via conventional RFLP, PCR, and SSR analysis. Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, SNPS and sequencing, all of which are conventional techniques.

As described herein, genes or coding sequences can be expressed in transformed plants. More particularly, plants can be genetically engineered to express various phenotypes of agronomic interest. A single gene or locus conversion or at least about 1, 2, 3, 4, 5, 6, 7, 8, 9, 10, 11, 12, 13, 14, 15, 16, 17, 18, 19, 20, 25, 30, 35 or 40 or more genes or locus conversions and less than about 100, 90, 80, 70, 60, 50, 40, 30, 20, 15, or 10 genes or locus conversions may be introduced into a plant or comprised in the genome of the wheat plant. Combinations or stacks of two or more genes or coding sequences described herein can be used. Through the transformation of wheat the expression of genes can be modulated to enhance disease resistance, insect resistance, herbicide resistance, water stress tolerance and agronomic traits as well as grain quality traits. These traits and the genes and organisms which may be targets are described in U.S. Pat. No. 8,809,554, which is incorporated herein by reference in its entirety for this purpose. Transformation can also be used to insert DNA sequences which control or help control male-sterility. DNA sequences native to wheat as well as non-native DNA sequences can be transformed into wheat and used to modulate levels of native or non-native proteins. The sequences can be heterologous comprising a coding sequence operably linked to a heterologous regulatory element, such as a promoter. Anti-sense technology, various promoters, targeting sequences, enhancing sequences, and other DNA sequences can be inserted into the wheat genome for the purpose of modulating the expression of proteins.

Exemplary genes which can be used include, but are not limited to, genes that confer resistance to pests such as Hessian fly, wheat stem sawfly, cereal leaf beetle, and/or green bug or disease, to pathogens *Cladosporium fulvum Pseudomonas syringae Fusarium graminearum* Schwabe, wheat rusts, *Septoria tritici, Septoria nodorum*, powdery mildew, *Helminthosporium* diseases, smuts, bunts, *Fusarium* diseases, bacterial diseases, and viral diseases.

Other genes, coding sequences or targets which can be used include those encoding *Bacillus thuringiensis* protein, a derivative thereof or a synthetic polypeptide modeled thereon. Examples of *Bacillus thuringiensis* transgenes encoding a endotoxin and being genetically engineered are given in the following patents and patent applications and hereby are incorporated by reference for this purpose: U.S. Pat. Nos. 5,188,960; 5,689,052; 5,880,275; 8,809,654; WO 91/14778; WO 99/31248; WO 01/12731; WO 99/24581; WO 97/40162 and U.S. application Ser. Nos. 10/032,717; 10/414,637; and Ser. No. 10/606,320.

Other genes, coding sequences or targets which can be used include those encoding an insect-specific hormone or pheromone such as an ecdysteroid and juvenile hormone, a variant thereof, a mimetic based thereon, or an antagonist or agonist thereof, an insect diuretic hormone receptor, such as an allostatin (see also U.S. Pat. No. 5,266,317 incorporated herein by reference for this purpose), an enzyme responsible for a hyper accumulation of a monterpene, a sesquiterpene, a steroid, hydroxamic acid, a phenylpropanoid derivative or another non-protein molecule with insecticidal activity, an enzyme involved in the modification, including the post-translational modification, of a biologically active molecule, for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic; a molecule that stimulates signal transduction, for example mung bean calmodulin cDNA clones and maize calmodulin cDNA clones; a hydrophobic peptide (see U.S. Pat. No. 5,580,852 and U.S. Pat. No. 5,607,914 incorporated herein by reference for this purpose); a membrane permease, a channel former or a channel blocker, for example, cropin-beta lytic peptide analog conferring *Pseudomonas solanacearum*; an insect-specific antibody or an immunotoxin derived therefrom, or a virus-specific antibody; a developmental-arrestive protein such as a endopolygalacturonase-inhibiting protein or a ribosome-inactivating gene; genes involved in the Systemic Acquired Resistance (SAR) Response and/or the pathogenesis related genes, In some embodiments, coat protein-mediated resistance can be conferred in plants against one or more of alfalfa mosaic virus, cucumber mosaic virus, tobacco streak virus, potato virus X, potato virus Y, tobacco etch virus, tobacco rattle virus and tobacco mosaic virus. Such resistance may be conferred using, for example, a viral-invasive protein or a complex toxin derived therefrom.

In some embodiments, genes, coding sequences or targets which can be used include, without limitation, antifungal genes (see, for example, US Publication No: 20020166141 incorporated herein by reference for this purpose); detoxification genes, such as for fumonisin, beauvericin, moniliformin and zearalenone and their structurally related derivatives (see, for example, U.S. Pat. No. 5,792,931 incorporated herein by reference for this purpose); cystatin and cysteine proteinase inhibitors (see for example, US Patent Publication Serial No: 20050102717 incorporated herein by reference for this purpose), defensin genes (see for example, PCT Public WO03000863 and US Patent Publication Serial No: 20030041348); and genes conferring resistance to nematodes, see for example, WO 03/033651.

Genes, coding sequences, or targets that confer resistance to a herbicide are described, for example, in U.S. Pat. No. 8,809,654, which is incorporated by reference herein for this purpose. Examples include genes or coding sequences encoding acetohydroxy acid synthase, a chimeric protein of rat cytochrome P4507A1, yeast NADPH-cytochrome P450 oxidoreductase, glutathione reductase, superoxide dismutase, phosphotransferases, ALS and AHAS enzymes and other genes or coding sequences which confer resistance to a herbicide such as an imidazalinone or a sulfonylurea (see also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, each of which are incorporated herein by reference for this purpose); Glyphosate or glufosinate resistance can also be conferred using, for example, sequences encoding mutant 5-enolpyruvl-3-phosphikimate synthase (EPSP), aroA genes, phosphinothricin acetyl transferase (PAT), glyphosate oxido-reductase enzyme, glyphosate N-acetyltransferase, glutamine synthetase, *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. Nos. 4,769,061, 4,975,374, 4,940,835, 5,776,760, 5,463,175, 5,627,061, 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; US Patent Publication No. 20040082770 and international publications EP1173580; WO 01/66704; EP1173581 and EP1173582, EP 0 242 246 and EP 0 242 236, each of which are incorporated herein by reference for this purpose. See also, U.S. Pat. Nos. 5,969,213; 5,489,520; 5,550,318; 5,874,265; 5,919,675; 5,561,236; 5,648,477; 5,646,024; 6,177,616; and 5,879,903, each of which are incorporated herein by reference for this purpose.

Triazine resistance can be conferred using, for example, psbA and gs+ genes, sequences encoding a benzonitrile (nitrilase gene) such as disclosed in U.S. Pat. No. 4,810,648 incorporated herein by reference for this purpose.

Resistance to herbicides which target Protoporphyrinogen oxidase (protox) can also be conferred such resistance being described in U.S. Pat. Nos. 6,288,306, 6,282,837, 5,767,373 and international publication WO 01/12825 the disclosures of each of which are herein incorporated by reference for this purpose.

Genes, coding sequences, or targets that confer or improve grain quality include, without limitation, altered fatty acids (for example, oleic, linoleic, linolenic), altered phosphorus content (for example, using phytase), altered carbohydrates such as modulating the branching pattern of starch or altering thioredoxin, *Bacillus subtilis* levansucrase gene, *Bacillus licheniformis* alpha-amylase, tomato invertase, alpha-amylase gene, starch branching enzyme II, UDP-D-xylose 4-epimerase, Fragile 1 and 2, Ref1, HCHL, C4H, high oil seed such as by modification of starch levels (AGP). Fatty acid modification genes mentioned above may also be used to affect starch content and/or composition through the interrelationship of the starch and oil pathways, altered content or composition of antioxidants such as tocopherol or tocotrienols, such as using a phytl prenyl transferase (ppt), or through alteration of a homogentisate geranyl geranyl transferase (hggt). Genes, coding sequences, or targets that can be targets to confer or improve grain quality are disclosed in, for example, see U.S. Pat. Nos. 8,809,654, 6,787, 683, 6,531,648, 6,423,886, 6,232,529, 6,197,561, 6,825,397, US Patent Publication Nos. 2003/0079247, US2003/0204870, US2004/0034886 international PCT publications WO 02/42424, WO 98/22604, WO 03/011015, WO02/057439, WO03/011015, WO 99/10498, WO 00/68393, and WO 03/082899.

Genes, coding sequences or targets for altered essential seed amino acids, such as one or more of lysine, methionine, threonine, tryptophan or altered sulfur amino acid content are also provided, can be used in the methods and plants described herein and are described in, for example, U.S. Pat. Nos. 8,809,654, 6,803,498, 6,127,600, 6,194,638, 6,346, 403, 6,080,913, 5,990,389, 5,939,599, 5,912,414, 5,850,016, 5,885,802, 5,885,801, 5,633,436, 5,559,223, 6,664,445, 6,459,019, 6,194,638, 6,399,859, 6,441,274, international PCT applications WO99/40209, WO99/29882, WO98/20133, WO96/01905, WO98/56935, WO98/45458, WO98/42831, WO95/15392, WO01/79516, WO00/09706, and US Publication Nos. U52003/0150014, US2003/0163838, US2004/0068767, and US2004/0025203, the disclosures of each of which are herein incorporated by reference in its entirety for these purposes.

Genes, coding sequences or targets that control or alter male sterility and methods for conferring male sterility and male sterile plants are provided. There are several methods of conferring genetic male sterility available, such as disclosed in U.S. Pat. Nos. 8,809,654, 4,654,465 and 4,727, 219, 3,861,709, 3,710,511, 5,432,068, the disclosures of each of which are herein incorporated by reference for this purpose. For additional examples of nuclear male and female sterility systems and genes, see also, U.S. Pat. No. 5,859,341; U.S. Pat. No. 6,297,426; U.S. Pat. No. 5,478,369; U.S. Pat. No. 5,824,524; U.S. Pat. No. 5,850,014; and U.S. Pat. No. 6,265,640; each of which are hereby incorporated by reference for this purpose.

Genes, coding sequences or targets that create a site for site specific DNA integration can also be used such as the introduction of FRT sites that may be used in the FLP/FRT system and/or Lox sites that may be used in the Cre/Loxp system. Other systems that may be used include the Gin recombinase of phage Mu, the Pin recombinase of *E. coli*, and the R/RS system of the pSR1 plasmid.

Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress are provided. For example, see: U.S. Pat. Nos. 8,809,654, 5,892,009, 5,965,705, 5,929,305, 5,891,859, 6,417,428, 6,664,446, 6,706,866, 6,717,034, 6,801,104, 6,177,275, 6,107,547, 6,084,153, US Patent Publication Nos. 2004/0148654, 2004/0237147, 2003/0166197, 2004/0128719, 2004/0098764, 2004/0078852, international PCT application WO2000060089, WO2001026459, WO2001035725, WO 00/73475; WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, WO01/36596 and WO9938977, WO2000/006341, WO04/090143, WO0202776, WO2003052063, WO0164898, and W0200032761, the disclosures of each of which are herein incorporated by reference in its entirety for this purpose.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. No. 6,794,560, U.S. Pat. No. 6,307,126 (GAI), WO99/09174 (D8 and Rht), and WO2004076638 and WO2004031349 (transcription factors), the disclosures of each of which are herein incorporated by reference.

Genes that confer agronomic enhancements, nutritional enhancements, or industrial enhancements can also be used. Such genes are described for example in U.S. Pat. No. 8,809,654, the disclosure of which is herein incorporated by reference in for this purpose. Such enhancements include, without limitation, improved tolerance to water stress from drought or high salt water condition. See e.g. U.S. Pat. Nos. 5,981,842, 5,780,709, international patent applications WO 92/19731, WO 92/19731 the disclosures of each of which is herein incorporated by reference for this purpose.

In some embodiments, methods of treating W040376U1 with a mutagen and the plant produced by mutagenesis of W040376U1 are provided. Backcross conversions of wheat variety W040376U1 are also described. A backcross conversion occurs when DNA sequences are introduced through traditional (non-transformation) breeding techniques, such as backcrossing. DNA sequences, whether naturally occurring or transgenes, may be introduced using these traditional breeding techniques. Desired traits transferred through this process include, but are not limited to, nutritional enhancements, industrial enhancements, disease resistance, insect resistance, herbicide resistance, agronomic enhancements, grain quality enhancement, waxy starch, breeding enhancements, seed production enhancements, and male sterility. Descriptions of some of the cytoplasmic male sterility genes, nuclear male sterility genes, chemical hybridizing agents, male fertility restoration genes, and methods of using the aforementioned are discussed in "Hybrid Wheat by K. A. Lucken (pp. 444-452 In *Wheat and Wheat Improvement*, ed. Heyne, 1987). Examples of genes for other traits which can be used with the methods, plants and plant parts described herein include: Leaf rust resistance genes (Lr series such as Lr1, Lr10, Lr21, Lr22, Lr22a, Lr32, Lr37, Lr41, Lr42, and Lr43), *Fusarium* head blight-resistance genes (QFhs.ndsu-3B and QFhs.ndsu-2A), Powdery Mildew resistance genes (Pm21), common bunt resistance genes (Bt-10), and wheat streak mosaic virus resistance gene (Wsm1), Russian wheat aphid resistance genes (Dn series such as Dn1, Dn2, Dn4, Dn5), Black stem rust resistance genes (Sr38), Yellow rust resistance genes (Yr series such as Yr1, YrSD, Yrsu, Yr17, Yr15, YrH52), Aluminum tolerance genes (Alt(BH)), dwarf genes (Rht), vernalization genes (Vrn), Hessian fly resistance genes (H9, H10, H21, H29), grain color genes (R/r), glyphosate resistance genes (EPSPS), glufosinate genes (bar, pat) and water stress tolerance genes (Hva1, mtID). The trait of interest is transferred from the donor parent to the recurrent parent, in this case, the wheat plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele requires growing and selfing the first backcross to determine which plants carry the recessive alleles. Recessive traits may require additional progeny testing in successive backcross generations to determine the presence of the gene of interest.

Methods of developing a backcross conversion W040376U1 wheat plant are provided including the step of repeated backcrossing to wheat variety W040376U1. The number of backcrosses made may be 2, 3, 4, 5, 6, 7, 8 or greater, and fewer than 50, 40, 30, 25, 20, 15, 10, 9, or 8. The specific number of backcrosses used will depend upon the genetics of the donor parent and whether molecular markers are utilized in the backcrossing program. Provided are plants and plant populations that are produced from backcrossing methods, transformation, locus conversion, or otherwise produced, and combinations thereof and that retain at least 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, 99.7%, 99.8%, or 99.9% or 99.95%, 99.98%, 99.985%, 99.99% or 99.995% of the genetic profile of wheat variety W040376U1. The percentage of the genetics retained in the backcross conversion may be measured by either pedigree analysis or through the use of genetic techniques such as molecular markers or electrophoresis. Such methods and techniques are described in U.S. Pat. No. 8,809,654, the disclosure of which is herein incorporated by reference for this purpose. The backcross conversion or locus conversion developed from this method may be similar to W040376U1 for the results listed in Table 1B. Such similarity may be measured by a side by side phenotypic comparison, with differences and similarities determined at a 5% significance level, when appropriate in environmental conditions that account for the trait being transferred. For example, herbicide should not be applied in the phenotypic comparison of herbicide resistant backcross conversion of W040376U1 when compared back to W040376U1.

Described are methods for using wheat variety W040376U1 in plant breeding and plants and plant populations produced by such methods. For example, wheat variety W040376U1 can be crossed with another variety of wheat to form a first generation population of F1 plants. This first generation population of F1 plants will comprise an essentially complete set of the alleles of wheat variety W040376U1. Also provided are methods and plants which use transgenic or backcross conversions of wheat variety W040376U1 to produce first generation F1 plants.

A method of developing a W040376U1-progeny wheat plant comprising crossing W040376U1 with a second wheat plant and performing a breeding method is also described.

An exemplary method for producing a line derived from wheat variety W040376U1 is as follows. Wheat variety W040376U1 is crossed with another variety of wheat, such as an elite variety. The F1 seed derived from this cross is grown to form a homogeneous population. The F1 seed contains one set of the alleles from variety W040376U1 and one set of the alleles from the other wheat variety. The F1 genome is 50% variety W040376U1 and 50% of the other elite variety. The F1 seed is grown and allowed to self, thereby forming F2 seed. On average the F2 seed would have derived 50% of its alleles from variety W040376U1 and 50% from the other wheat variety, but various individual plants from the population can have a much greater percentage of their alleles derived from W040376U1. The F2 seed is grown and selection of plants made based on visual observation and/or measurement of traits. The W040376U1-derived progeny that exhibit one or more of the desired W040376U1-derived traits are selected and each plant is harvested separately. This F3 seed from each plant is grown in individual rows and allowed to self. Then selected rows or plants from the rows are harvested and threshed individually. The selections based on visual observation and/or measurements for desirable traits of the plants, such as one or more of the desirable W040376U1-derived traits are made. The process of growing and selection is repeated any number of times until a homozygous W040376U1-derived wheat plant is obtained. The homozygous W040376U1-derived wheat plant contains desirable traits derived from wheat variety W040376U1, some of which may not have been expressed by the other original wheat variety to which wheat variety W040376U1 was crossed and some of which may have been expressed by both wheat varieties but now would be at a level equal to or greater than the level expressed in wheat variety W040376U1. The homozygous W040376U1-derived wheat plants have, on average, 50% of their genes derived from wheat variety W040376U1, but various individual plants from the population would have a much greater percentage of their alleles derived from W040376U1. The breeding process, of crossing, selfing, and selection may be repeated to produce another population of W040376U1-derived wheat plants with, on average, 25% of their genes derived from wheat variety W040376U1, and with various individual plants from the population having a much greater percentage of their alleles derived from W040376U1. Homozygous W040376U1-derived wheat plants that have received W040376U1-derived traits are also provided.

In some instances, selection may or may not occur at every selfing generation, selection may occur before or after the actual self-pollination process occurs, or individual selections may be made by harvesting individual spikes, plants, rows or plots at any point during the breeding process described herein. In addition, double haploid breeding methods may be used at any step in the process. In one aspect, the population of plants produced at each and any generation of selfing, each such population consisting of plants containing approximately 50% of its genes from wheat variety W040376U1, 25% of its genes from wheat variety W040376U1 in the second cycle of crossing, selfing, and selection, 12.5% of its genes from wheat variety W040376U1 in the third cycle of crossing, selfing, and selection, and so on.

Also disclosed are methods of obtaining a homozygous W040376U1-derived wheat plant by crossing wheat variety W040376U1 with another variety of wheat and applying double haploid methods to the F1 seed or F1 plant or to any generation of W040376U1-derived wheat obtained by the selfing of this cross.

Still further, methods for producing W040376U1-derived wheat plants are provided by crossing wheat variety W040376U1 with a wheat plant and growing the progeny seed, and repeating the crossing or selfing along with the growing steps with the W040376U1-derived wheat plant from 1 to 2 times, 1 to 3 times, 1 to 4 times, or 1 to 5 times. Thus, any and all methods using wheat variety W040376U1 in breeding, including selfing, pedigree breeding, backcrossing, hybrid production and crosses to populations are provided. Unique starch profiles, molecular marker profiles and/or breeding records can be used to identify the progeny lines or populations derived from these breeding methods.

Also disclosed are methods of harvesting the grain of variety wheat variety W040376U1 and using the grain as seed for planting. Embodiments include cleaning the seed, treating the seed, and/or conditioning the seed. Cleaning the seed includes removing foreign debris such as weed seed and removing chaff, plant matter, from the seed. Conditioning the seed can include controlling the temperature and rate of dry down and storing seed in a controlled temperature environment. Seed treatment is the application of a composition to the seed such as a coating or powder. Seed material can be treated, typically surface treated, with a composition comprising combinations of chemical or biological herbicides, herbicide safeners, pesticides, insecticides, fungicides, nutrients, germination inhibitors, germination promoters, cytokinins, nutrients, plant growth regulators, antimicrobials, and activators, bactericides, nematicides, avicides, or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., published by the British Crop Production Council. Some specific seed treatments that may be used on crop seed include, but are not limited to, abscisic acid, acibenzolar-S-methyl, avermectin, amitrol, azaconazole, azospirillum, azoxystrobin, *bacillus, Bacillus subtilis, Bacillus simplex, Bacillus firmus, Bacillus amyloliquefaciens, Pasteuria* genus (e.g. *P. nishizawae*), bradyrhizobium, captan, carboxin, chitosan, clothianidin, copper, cyazypyr, difenoconazole, etidiazole, fipronil, fludioxonil, fluquinconazole, flurazole, fluxofenim, GB126, Harpin protein, imazalil, imidacloprid, ipconazole, isofavenoids, lipo-chitooligosaccharide, mancozeb, manganese, maneb, mefenoxam, metalaxyl, metconazole, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendaxole, thiamethoxam, thiocarb, thiram, tolclofos-methyl, triadimenol, *trichoderma*, trifloxystrobin, triticonazole and/or zinc.

It is routine practice to test seed varieties and seeds with specific genetic resistance traits to determine which seed treatment options and application rates will complement such varieties and genetic resistance traits in order to enhance yield. For example, a variety with good yield potential but loose smut susceptibility will benefit from the use of a seed treatment that provides protection against loose smut. Likewise, a variety encompassing a genetic resistance trait conferring insect resistance will benefit from the second mode of action conferred by the seed treatment. Further, the good root establishment and early emergence that results from the proper use of a seed treatment will result in more efficient nitrogen use, a better ability to withstand drought and an overall increase in yield potential of a variety or varieties containing a certain trait when combined with a seed treatment.

Methods for analyzing polynucleotides from plants, plant parts or seeds described herein may include contacting a polynucleotide from the plant, plant part or seed, such as from wheat variety W040376U1 with a molecular marker or with modified nucleotides that facilitate sequencing of the polynucleotide. The polynucleotide may be isolated, separated or otherwise obtained from the plant, plant part or seed. Modified nucleotides such as dNTPs may be incorporated with the polynucleotides along with appropriate primers in a reaction mixture that facilitates sequencing. Sequencing can be done using any method known in the art.

It will be apparent to those of skill in the art that variations may be applied to the compositions and methods described herein and in the steps or in the sequence of steps of the method described herein without departing from the concept, spirit and scope of the invention. More specifically, it will be apparent that certain changes and modifications such as single gene conversions, including for example, modifications and mutations, somoclonal variants, variant individuals selected from large populations of the plants of the instant inbred and the like may be practiced. All such similar substitutes and modifications apparent to those skilled in the art are deemed to be within the spirit, scope and concept of the invention.

It is to be understood that the invention is not limited in its application to the details of construction and the arrangement of components set forth in the following description. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications are herein expressly incorporated by reference in their entirety for all purposes to the same extent as if each individual publication or patent application was specifically and individually incorporated by reference. In case of conflict between the present disclosure and the incorporated patents, publications and references, the present disclosure should control.

EXAMPLES

Example 1

Performance of W040376U1

In the examples that follow, the traits and characteristics of wheat variety W040376U1 are given in paired comparisons with another variety during the same growing conditions and same year. The data collected on each wheat variety is presented for a number of characteristics and traits (Table 2, Table 3, and Table 4).

The results in Table 2 compare variety W040376U1 to varieties 25R78, 25R51, and 25R47 for various agronomic traits. Data in Table 2 was collected at locations in Arkansas, Georgia, Illinois, Indiana, Kentucky, Michigan, Missouri, Mississippi, North Carolina, Ohio, Virginia and Ontario, Canada. The results in Table 3 compare variety W040376U1 to varieties 25R78, 25R51, and 25R47 for various disease resistance traits. Data in Table 3 was collected at locations in Arkansas, Georgia, Illinois, Indiana, Kentucky, Michigan, Missouri, Mississippi, North Carolina, Ohio, Virginia and Ontario, Canada. The results in Table 4 show values for the grain quality of variety W040376U1 and comparison varieties 25R78, 25R51 and 25R47. Quality data were collected from 2011-2013 at the USDA ARS Soft Wheat Quality Lab in Wooster, Ohio.

TABLE 2

Agronomic trait paired comparisons of W040376U1 during the period 2010-2013.

| | Variety | | | | | |
| --- | --- | --- | --- | --- | --- | --- |
| | Grain Yield bu/ac | Test Weight lb/bu | Heading Date After Jan 1 | Winter hardiness 1-9@ | Plant Height cm | Straw Lodging 1-9@ |
| 2010, 2012-2013 | | | | | | |
| W040376U1 | 93.8 | 57.8 | 122.0 | 7.0 | 91.4 | 6.0 |
| 25R78 | 92.7 | 58.3 | 120.0 | 5.0 | 88.9 | 7.0 |
| Locations | 42 | 42 | 9 | 2 | 10 | 3 |
| Reps. | 81 | 79 | 15 | 4 | 16 | 6 |
| Prob. | 0.3661 | 0.0698 | 0.0084 | 0.2048 | 0.003 | 0.1296 |

TABLE 2-continued

Agronomic trait paired comparisons of W040376U1 during the period 2010-2013.

| | Variety | | | | | |
|---|---|---|---|---|---|---|
| | Grain Yield bu/ac | Test Weight lb/bu | Heading Date After Jan 1 | Winter hardiness 1-9@ | Plant Height cm | Straw Lodging 1-9@ |
| 2012 | | | | | | |
| W040376U1 | 96.6 | 59.6 | 115.0 | | 88.9 | |
| 25R51 | 100.1 | 59.7 | 113.0 | | 91.4 | |
| Locations | 12 | 12 | 2 | | 1 | |
| Reps. | 24 | 24 | 4 | | 2 | |
| Prob. | 0.2346 | 0.5290 | 0.1257 | | 0 | |
| 2010-2013 | | | | | | |
| W040376U1 | 93.7 | 58.2 | 124.0 | 7.0 | 91.4 | 6.0 |
| 25R47 | 96.1 | 56.4 | 124.0 | 7.0 | 86.4 | 6.0 |
| Locations | 53 | 54 | 11 | 2 | 11 | 6 |
| Reps. | 97 | 96 | 19 | 4 | 18 | 11 |
| Prob. | 0.0357 | 0.0000 | 1.0000 | 1.0000 | 0.0009 | 0.0108 |

@ Scale of 1-9 where 9 = excellent or resistant, 1 = poor or susceptible.

@ Scale of 1-9 where 9=excellent or resistant, 1=poor or susceptible.
Data in above table collected at locations in Arkansas, Georgia, Illinois, Indiana, Kentucky, Michigan, Missouri, Mississippi, North Carolina, Ohio, Virginia and Ontario, Canada.

TABLE 3

Disease trait paired comparisons of W040376U1 during the period 2010-2013.

| | Variety | | | | | |
|---|---|---|---|---|---|---|
| | Scab 1-9@ | Leaf Rust 1-9@ | Stripe Rust 1-9@ | Leaf Blight 1-9@ | Powdery Mildew 1-9@ | SBMV 1-9@ |
| 2010, 2012-2013 | | | | | | |
| W040376U1 | 8.0 | 5.0 | 7.0 | 5.0 | 6.0 | 3.0 |
| 25R78 | 3.0 | 8.0 | 4.0 | 3.0 | 5.0 | 7.0 |
| Locations | 6 | 8 | 7 | 2 | 4 | 2 |
| Reps. | 10 | 14 | 13 | 4 | 5 | 4 |
| Prob. | 0.0006 | 0.0037 | 0.0018 | 1.0000 | 0.0577 | 0.0792 |
| 2012 | | | | | | |
| W040376U1 | 8.0 | 5.0 | 7.0 | | | |
| 25R51 | 7.0 | 8.0 | 7.0 | | | |
| Locations | 1 | 2 | 5 | | | |
| Reps. | 2 | 4 | 10 | | | |
| Prob. | | 0.4296 | 0.3739 | | | |
| 2010-2013 | | | | | | |
| W040376U1 | 8.0 | 5.0 | 7.0 | 5.0 | 6.0 | 3.0 |
| 25R47 | 4.0 | 5.0 | 8.0 | 6.0 | 5.0 | 6.0 |
| Locations | 9 | 8 | 7 | 2 | 4 | 3 |
| Reps. | 14 | 14 | 13 | 4 | 5 | 5 |
| Prob. | 0.0000 | 0.5693 | 0.0186 | 0.2952 | 0.0609 | 0.0820 |

@ Scale of 1-9 where 9 = excellent or resistant, 1 = poor or susceptible. SBMV = Soil-borne Mosaic Virus.

@ Scale of 1-9 where 9=excellent or resistant, 1=poor or susceptible.
SBMV=Soil-borne Mosaic Virus.
Data in above table collected at locations in Arkansas, Georgia, Illinois, Indiana, Kentucky, Michigan, Missouri, Mississippi, North Carolina, Ohio, Virginia and Ontario, Canada.

TABLE 4

Average Soft wheat quality data, 2011-2013.

| Variety | Flour Yield % | Break Flour Yield % | Flour Protein % | Sucrose SRC % | Lactic Acid SRC % |
|---|---|---|---|---|---|
| 2012-2013 | | | | | |
| W040376U1 | 67.0 | 38.8 | 6.8 | 92.6 | 91.8 |
| 25R78 | 70.3 | 39.3 | 7.4 | 90.4 | 85.1 |
| Years | 2 | 2 | 2 | 2 | 2 |
| Reps. | 2 | 2 | 2 | 2 | 2 |
| Prob. | 0.1207 | 0.8000 | 0.3033 | 0.6115 | 0.0944 |
| 2012 | | | | | |
| W040376U1 | 68.6 | 43.9 | 6.7 | 90.7 | 85.9 |
| 25R51 | 69.7 | 40.5 | 7.6 | 86.2 | 74.7 |
| Years | 1 | 1 | 1 | 1 | 1 |
| Reps. | 1 | 1 | 1 | 1 | 1 |
| Prob. | | | | | |
| 2011-2013 | | | | | |
| W040376U1 | 67.1 | 40.5 | 6.6 | 90.5 | 88.8 |
| 25R47 | 71.2 | 46.0 | 6.9 | 83.9 | 87.3 |
| Years | 3 | 3 | 3 | 3 | 3 |
| Reps. | 3 | 3 | 3 | 3 | 3 |
| Prob. | 0.0029 | 0.0300 | 0.3261 | 0.0036 | 0.6289 |

Lactic Acid SRC = Lactic Acid Solvent Retention Capacity
Sucrose SRC = Sucrose solution Retention Capacity
Quality data collected at the USDA-ARS Soft Wheat Quality Lab in Wooster, OH Lactic Acid SRC=Lactic Acid Solvent Retention Capacity
Sucrose SRC=Sucrose solution Retention Capacity
Quality data collected at the USDA-ARS Soft Wheat Quality Lab in Wooster, Ohio Examples 2-13

Assays Performed to Develop W040376U1

The following examples provide descriptions of several assays that can be used to characterize and/or select a wheat variety during one or more stages of variety development. Many other methods and assays are available and can be substituted for, or used in combination with, one or more of the examples provided herein. Tables 1, 2, 3 and 4 provide further information on wheat variety W040376U1, which results may be produced from at least one or more assays or methods described in the following examples.

Example 2

Stripe Rust Screening

Stripe rust is a fungal leaf disease that is most common in the mid-southern United States in the early spring. Significant levels of the disease can be found in some seasons anywhere in North America. The infection often mostly occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 3

Leaf Rust Screening

Leaf rust is a fungal leaf disease that is most common in the southern United States in the spring and early summer. Significant levels of the disease can be found in most seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 4

Leaf Blight Screening

Fungal leaf blights, including Tan spot, *Septoria tritici* blotch, and *Stagnospora nodorum* blotch, are common in much of the North American wheat growing regions. The infection is most damaging when it occurs on the flag leaf but it may attack the entire plant, including the head. Natural infection of plants in the field may be rated visually using a 1-9 scale, where 1 indicates complete susceptibility and 9 indicates complete resistance.

Example 5

Scab Screening

*Fusarium* head blight or scab is a fungal disease that is common in much of the North American wheat growing regions. Infection occurs during flowering and is most severe when conditions are wet, warm and remain humid. The disease infects flowers on the spike and will spread to adjacent flowers, often infecting most of the developing kernels on the spike. Natural infection of plants in the field may be rated visually using a 1-9 scale, where 1 indicates complete susceptibility and 9 indicates complete resistance. Infection may be induced in controlled screening experiments where spikes are inoculated with specific spore concentrations of the fungus by spraying the spikes at flowering or injecting the inoculum directly into a flower on each spike. There are also molecular markers for QTL linked to some specific resistance genes.

Example 6

Powdery Mildew Screening

Powdery mildew is a fungal leaf disease that is most common in the southern United States in the spring and early summer. Significant levels of the disease can be found in many seasons anywhere in North America. The infection is most damaging when it occurs on the flag leaf but it may attack the entire plant, including the head. Natural infection of plants in the field may be rated visually using a 1-9 scale, where 1 indicates complete susceptibility and 9 indicates complete resistance. Some major genes for resistance may be detected using controlled seedling screening experiments inoculated with specific races of the pathogen. There are also molecular markers for QTL linked to some specific resistance genes.

Example 7

Soilborne Mosaic Virus Screening

Soilborne mosaic virus is transmitted by the vector, *Polymyxa graminis*, which tends to be most common in low-lying, wet soils; particularly those frequently grown to wheat. Symptoms appear in the spring as light green to yellow mottling along with stunting and resetting plant growth in the most susceptible varieties. Natural infection of plants in the field may be rated visually using a 1-9 scale, where 1 indicates complete susceptibility and 9 indicates complete resistance. Higher levels of natural infection can be induced for screening by planting wheat annually in the same field to increase the vector level.

Example 8

Wheat Yellow (Spindle Streak) Mosaic Virus Screening

Wheat yellow virus is transmitted by the vector, *Polymyxa graminis*, and is most common during cool weather conditions in the spring. Symptoms appear as light green to yellow streaks and dashes parallel to the leaf veins. Symptoms often fade prior to heading as weather conditions become warmer. Natural infection of plants in the field may be rated visually using a 1-9 scale, where 1 indicates complete susceptibility and 9 indicates complete resistance.

Example 9

Flour Yield Screening

The potential average flour yield of wheat can be determined on samples of grain that has been cleaned to standard and tempered to uniform moisture, using a test mill such as the Allis-Chalmers or Brabender mill. Samples are milled to established parameters, the flour sifted into fractions, which are then weighed to calculate flour yield as a percentage of grain weight.

Flour yield "as is" is calculated as the bran weight (over 40 weight) subtracted from the grain weight, divided by grain weight and times 100 to equal "as is" flour yield. Flour yield is calculated to a 15% grain moisture basis as follows: flour moisture is regressed to predict the grain moisture of the wheat when it went into the Quad Mill using the formula Initial grain moisture=1.3429×(flour moisture)−4.

The flour yields are corrected back to 15% grain moisture after estimating the initial grain moisture using the formula Flour Yield$_{(15\%)}$=Flour Yield$_{(as\ is)}$−1.61%×(15%−Actual flour moisture)

Example 10

Flour Protein Screening

The protein content as a percentage of total flour may be estimated by the Kjeldahl method or properly calibrated near-infrared reflectance instruments to determine the total nitrogen content of the flour.

Flour protein differences among cultivars can be a reliable indicator of genetic variation provided the varieties are grown together, but can vary from year to year at any given location. Flour protein from a single, non-composite sample may not be representative. Based on the Soft Wheat Quality Laboratory grow-outs, protein can vary as much 1.5% for a cultivar grown at various locations in the same ½ acre field.

Example 11

Sucrose Solvent Retention Capacity (SRC)

The solvent retention capacity (SRC) of wheat flour measures the ability of the flour to retain various solvents after centrifugation. Sucrose SRC predicts the starch damage and pentosan components, and can be correlated to sugar-snap cookie diameter quality metrics.

Sucrose SRC is a measure of arabinoxylans (also known as pentosans) content, which can strongly affect water absorption in baked products. Water soluble arabinoxylans are thought to be the fraction that most greatly increases sucrose SRC. Sucrose SRC probably is the best predictor of cookie quality, with sugar snap cookie diameters decreasing by 0.07 cm for each percentage point increase in sucrose SRC. The negative correlation between wire-cut cookie and sucrose SRC values is r=−0.66 (p<0.0001). Sucrose SRC typically increases in wheat samples with lower flour yield (r=−0.31) and lower softness equivalent (r=−0.23). The cross hydration of gliadins by sucrose also causes sucrose SRC values to be correlated to flour protein (r=0.52) and lactic acid SRC (r=0.62). Soft wheat flours for cookies typically have a target of 95% or less when used by the US baking industry for biscuits and crackers. Sucrose SRC values increase by 1% for every 5% increase in lactic acid SRC. The 95% target value can be exceeded in flour samples where a higher lactic acid SRC is required for product manufacture since the higher sucrose SRC is due to gluten hydration and not to swelling of the water soluble arabinoxylans.

Example 12

Lactic Acid SRC

Lactic Acid SRC=Lactic Acid Solvent Retention Capacity. Lactic acid SRC measures gluten strength. Typical values are below 85% for "weak" soft varieties and above 105% or 110% for "strong" gluten soft varieties. See the above discussion of protein quality in this section for additional details of the lactic acid SRC. Lactic acid SRC results correlate to the SDS-sedimentation test. The lactic acid SRC is also correlated to flour protein concentration, but the effect is dependent on genotypes and growing conditions. The SWQL typically reports a protein-corrected lactic acid SRC value to remove some of the inherent protein fluctuation not due to cultivar genetics. Lactic acid is corrected to 9% protein using the assumption of a 7% increase in lactic acid SRC for every 1% increase in flour protein. On average across 2007 and 2008, the change in lactic acid SRC value was closer to 2% for every 1% protein.

Example 13

Molecular Screening

As shown in Table 1B, plants were analyzed at various times throughout the development of W040376U1 for specific alleles for scab resistance. As discussed above, and as is known to those skilled in the art, other traits can also be screened by molecular analysis.

DEPOSIT

Applicant has made a deposit of at least 2500 seeds of Wheat Variety W040376U1 with the American Type Culture Collection (ATCC), 10801 University Boulevard, Manassas, Va. 20110 USA, ATCC Deposit No. PTA-123400. The seeds deposited with the ATCC on Aug. 1, 2016 were taken from the seed stock maintained by Pioneer Hi-Bred International, Inc., 7249 NW 62$^{nd}$ Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R. §1.808. This deposit of the Wheat Variety W040376U1 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.). Unauthorized seed multiplication is prohibited.

The foregoing invention has been described in detail by way of illustration and example for purposes of clarity and understanding. However, it will be obvious that certain changes and modifications such as single locus modifications and mutations, somaclonal variants, variant individuals selected from large populations of the plants of the instant variety and the like may be practiced.

The scope of the claims should not be limited by the preferred embodiments set forth in the examples, but should be given the broadest interpretation consistent with the description as a whole.

All publications, patents and patent applications mentioned in the specification are indicative of the level of those skilled in the art to which this invention pertains.

What is claimed is:

1. A plant, plant part, seed, or plant cell of wheat variety W040376U1, representative seed of said variety having been deposited under ATCC accession number PTA-123400.

2. A wheat seed produced from the crossing of the plant or plant part of claim 1 with a different wheat plant or plant part.

3. A wheat plant or plant part produced by growing the wheat seed of claim 2.

4. A method for producing a second wheat plant comprising applying plant breeding techniques to the wheat plant or plant part of claim 3, wherein application of said techniques results in the production of a second wheat plant.

5. A method for producing a progeny seed comprising crossing the wheat plant of claim 3, to a plant of wheat variety W040376U1, representative seed of said variety having been deposited under ATCC accession number PTA-123400 and producing a progeny seed.

6. The method of claim 5 further comprising crossing a plant grown from the progeny seed of claim 5 to a plant of wheat variety W040376U1 and producing a backcrossed seed.

7. The backcrossed seed produced by claim 6.

8. A method for producing a double haploid wheat plant or plant part comprising a) crossing the wheat plant of claim 3, to another plant to form haploid cells; b) doubling the chromosomes of said haploid cells to form double haploid cells; and c) growing said double haploid cells into a double haploid wheat plant or plant part.

9. A method comprising cleaning the seed of claim 1.

10. A method comprising conditioning the seed of claim 1.

11. A method comprising applying a seed treatment to the seed of claim 1.

12. Flour produced by milling the seed of claim 1.

13. A tissue culture of cells produced from the plant, plant part, seed, or plant cell of claim 1.

14. A wheat plant regenerated from the tissue culture of claim 13.

15. A wheat plant comprising a transgene wherein said wheat plant was produced by transforming the plant, plant part, seed, or cell of claim 1.

16. A plant, plant part, seed, or plant cell of wheat variety W040376U1, representative seed of said variety having been deposited under ATCC accession number PTA-123400, further comprising a locus conversion.

17. The plant, plant part, seed, or plant cell of claim 16, wherein the locus conversion confers a trait selected from the group consisting of male sterility, abiotic stress tolerance, altered phosphorus, altered antioxidants, altered fatty acids, altered essential amino acids, altered carbohydrates, herbicide resistance, insect resistance and disease resistance.

18. A wheat seed produced by crossing the plant of claim 16 with a different wheat plant.

19. A wheat plant produced by growing the wheat seed of claim 18.

20. A method for producing a second wheat plant comprising applying plant breeding techniques to the wheat plant of claim 19, wherein application of said techniques results in the production of a second wheat plant.

* * * * *